(12) United States Patent
Stoutenburg et al.

(10) Patent No.: US 6,868,348 B1
(45) Date of Patent: Mar. 15, 2005

(54) ADAPTIVE HIGH FREQUENCY ENERGY DETECTION

(75) Inventors: Donn V. Stoutenburg, Westerville, OH (US); Ming Xu, Worthington, OH (US)

(73) Assignee: Entek IRD International Corporation, Milford, OH (US)

( * ) Notice: Subject to any disclaimer, the term of this patent is extended or adjusted under 35 U.S.C. 154(b) by 0 days.

(21) Appl. No.: 09/430,077

(22) Filed: Oct. 29, 1999

(51) Int. Cl.$^7$ .......................... G01F 17/00; G01F 23/00
(52) U.S. Cl. ...................................................... 702/56
(58) Field of Search ............................ 702/34, 56, 182, 702/183; 340/679, 680, 683, 17; 700/174, 175; 73/579, 609, 660

(56) References Cited

U.S. PATENT DOCUMENTS

| | | | |
|---|---|---|---|
| 3,895,343 A | | 7/1975 | Farr |
| 4,352,293 A | | 10/1982 | Kurihara et al. |
| 4,885,724 A | | 12/1989 | Read et al. |
| 4,894,644 A | | 1/1990 | Thomas |
| 5,109,700 A | | 5/1992 | Hicho |
| 5,216,921 A | | 6/1993 | Tsuboi |
| 5,407,265 A | | 4/1995 | Hamidieh et al. |
| 5,412,985 A | * | 5/1995 | Garcia et al. ................. 73/460 |
| 5,477,730 A | | 12/1995 | Carter |
| 5,511,422 A | * | 4/1996 | Hernandez ..................... 73/593 |
| 5,571,966 A | * | 11/1996 | Tsuboi ........................... 73/579 |
| 5,579,232 A | * | 11/1996 | Tong et al. .................... 700/175 |
| 5,633,811 A | * | 5/1997 | Canada et al. ................. 702/56 |
| 5,686,669 A | * | 11/1997 | Hernandez et al. ........... 73/660 |
| 5,687,735 A | | 11/1997 | Forbes et al. |
| 5,808,903 A | | 9/1998 | Schiltz et al. |
| 5,847,658 A | * | 12/1998 | Irie et al. ..................... 340/683 |
| 5,852,793 A | | 12/1998 | Board et al. |
| 5,854,994 A | * | 12/1998 | Canada et al. ................. 702/56 |
| 5,943,634 A | * | 8/1999 | Piety et al. .................... 702/56 |
| 5,995,910 A | * | 11/1999 | Discenzo ....................... 702/56 |
| 6,199,018 B1 | * | 3/2001 | Quist et al. ................... 702/34 |
| 6,260,004 B1 | * | 7/2001 | Hays et al. ................... 702/183 |
| 6,275,781 B1 | * | 8/2001 | Maness et al. ................ 702/182 |
| 6,301,572 B1 | * | 10/2001 | Harrison ....................... 706/52 |
| 6,321,602 B1 | * | 11/2001 | Ben-Romdhane ............ 73/660 |

FOREIGN PATENT DOCUMENTS

| | | |
|---|---|---|
| WO | WO96/35250 | 11/1996 |

OTHER PUBLICATIONS

Robinson et al., *Peak Value (Peak Value™) Analysis: Advantageous Over Demodulation for Gearing Systems and Slow Spead Bearings*, Presented at Piedmont Chapter of Vibration Institute; Charlotte, NC, Dec. 1, 1999.

* cited by examiner

*Primary Examiner*—John Barlow
*Assistant Examiner*—Demetrius Pretlow
(74) *Attorney, Agent, or Firm*—Wood Herron & Evans LLP; Alexander M. Gerasimow

(57) ABSTRACT

A data collector having a digital signal processing circuit that receives a digitized vibration signal, and performs processing steps to isolate high frequency pulses in the digitized vibration signal and quantify energy content of those pulses by detecting a peak negative value of the digitized peak-to-peak amplitude of the received vibration signal, and then using this peak negative value to compute a maximum peak-to-peak value of the received vibration signal. Periodically, the maximum peak-to-peak value and peak negative value are reduced in magnitude by a decay factor, such that the peak negative value and maximum peak-to-peak value decay over time. The decay factors used in computing the maximum peak-to-peak value and peak negative value are determined by the digital signal processing circuit and may be readily changed. As a consequence, high frequency processing performed by the digital signal processing circuit may be readily adapted to the particular frequency characteristics of the machine being analyzed for predictive maintenance, without modification of the analog circuitry of the data collector. The resulting maximum peak-to-peak value comprises a peak-detected digital output signal that may be stored and/or displayed to a user as a reflection of the high frequency content of the vibration signal, or frequency transformed for storage and/or display to a user.

31 Claims, 3 Drawing Sheets

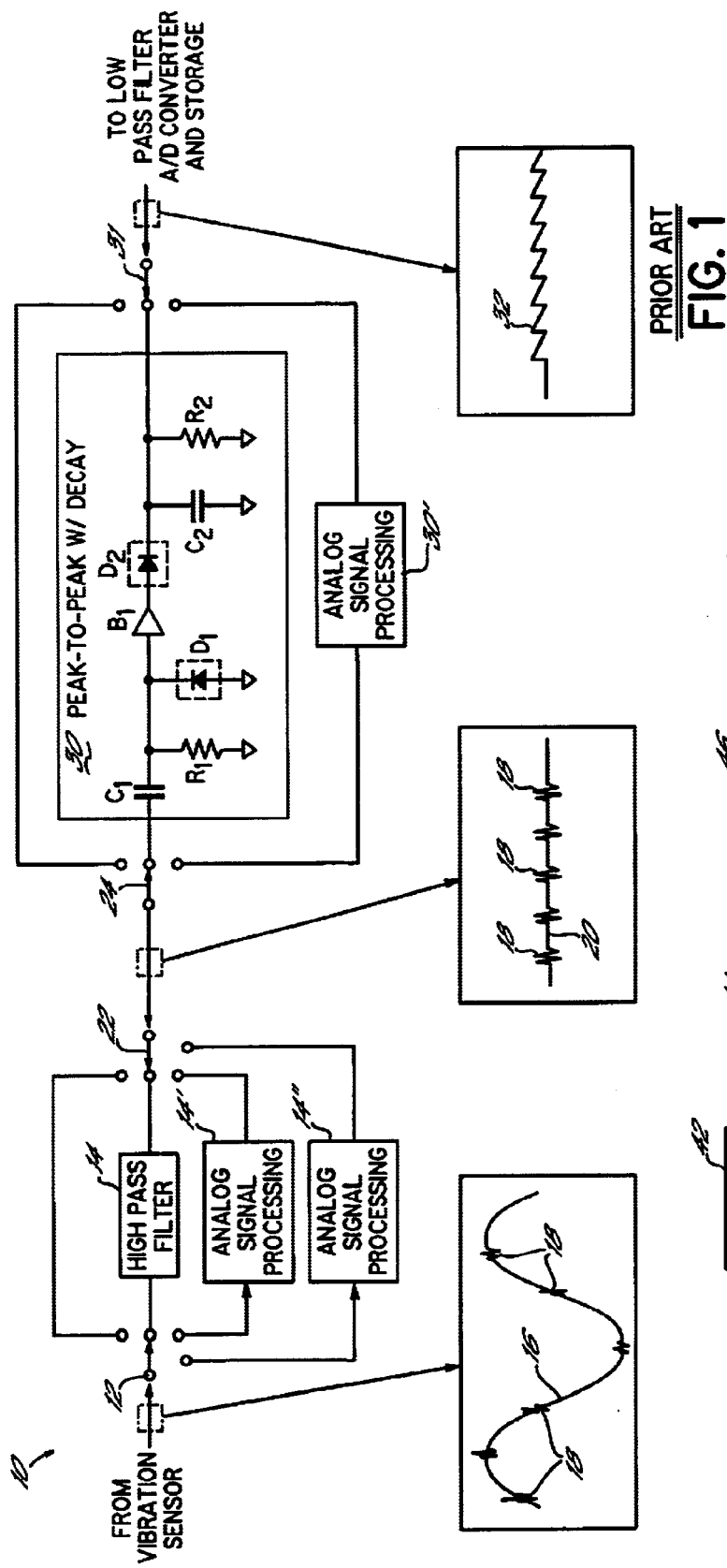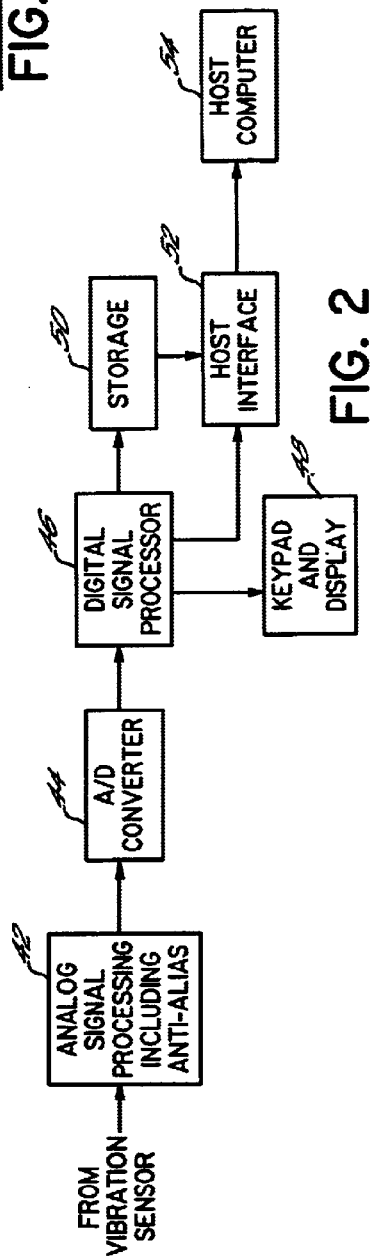
PRIOR ART
FIG. 1
FIG. 2

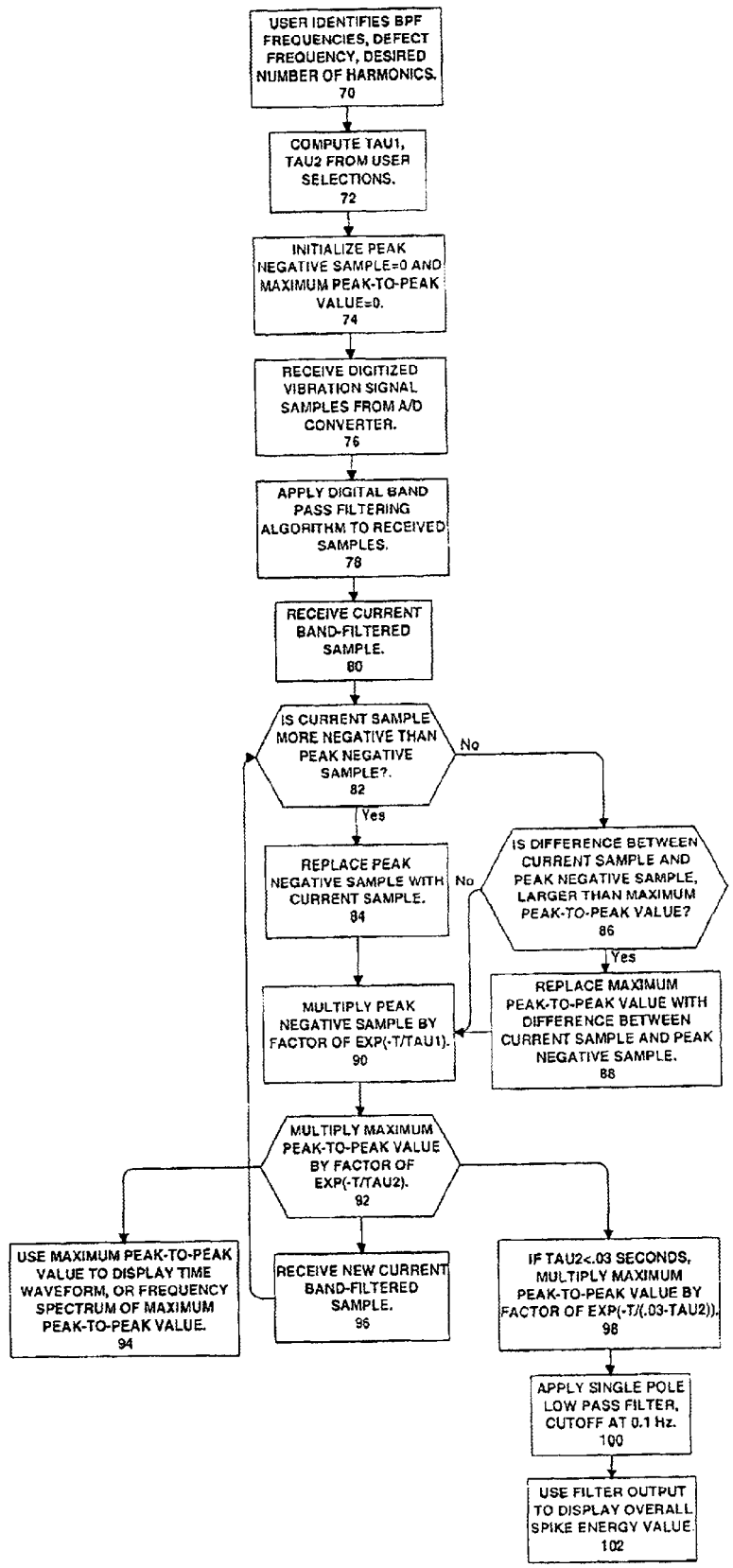

US 6,868,348 B1

ADAPTIVE HIGH FREQUENCY ENERGY DETECTION

FIELD OF THE INVENTION

The invention relates to collection and analysis of vibration data for the purposes of predictive maintenance.

BACKGROUND OF THE INVENTION

There are many well known methods for collecting vibration data for performing predictive maintenance. Typically, in these methods a vibration sensor such as a piezoelectric accelerometer is mechanically coupled to the machine to be monitored. The vibration sensor collects vibrations from the machine and converts these vibration to an electrical signal. The electrical signal is processed by suitable signal processing and converted from analog to digital form. The resulting digital signal is stored for later analysis.

Analysis of a vibration signal from a machine typically involves one or both of (1) comparing that signal to previously collected signals to identify an variations that would be indicative of machine wear and possible impending failure, and (2) forming a frequency spectrum of the vibration signal and evaluating this spectrum for patterns indicative of potential failures. Typically these operations are performed through the use of a data collector. A data collector includes analog signal processing electronics for receiving a vibration signal and conditioning that signal, and an analog to digital converter for digitally sampling the analog signal so that it may be stored and analyzed. Signal analysis may be performed using the data collector itself or by uploading collected and digitized signals from the data collector to a host computer where signal analysis is performed.

Typically the analog front end of a data collector includes a number of selectable analog signal conditioning circuits, each selectable by controlling an analog switch for connecting the element into the signal path through the data collector. As seen in FIG. 1, a typical data collector might include a first signal conditioning section in which analog switches 12 and 22 may be used to selectively pass the incoming analog signal through a high pass filter 14 or other analog signal processing blocks 14' and 14" (these blocks may include, e.g., low pass or band pass filters). Furthermore, a second signal conditioning section in the data collector might include additional analog switches 24 and 31 for selectively connecting the incoming vibration signal through a peak detecting circuit 30 or another analog signal processing circuit 30'. After these processing blocks, the signal may be further conditioned, and low pass filtered, and then converted from analog to digital form by an analog to digital converter, and stored in a digital memory.

As an example of the kinds of analysis performed with a data collector, consider a rotating machine that generates vibration signals at a fundamental frequency that corresponds to the frequency of rotation of the machine. During normal operation, additional vibration signals will be generated at higher frequencies as well. These higher frequency vibrations correspond to interactions of mechanical parts while the machine rotates, such as movements of moving parts in bearings, sliding pistons and cams, resonances of machine components, and other normal mechanical activity attendant to rotation of the machine. If, however, a bearing or other mechanical system begins to fail, the part will begin to generate different frequency patterns. For example, a bearing may develop a crack, causing a "click" to occur each time weight is applied to the crack in the bearing, which will be reflected as increased higher frequency vibration in a vibration signal from the machine. Alternatively, a sliding mechanical part may begin to fail and scrape undesirably as it moves, again causing increased higher frequency vibration.

It will be noted that collection and analysis of high frequency energy in a vibration signal is often critical in predictive maintenance analysis. For this reason, various techniques have been developed for isolating high frequency pulses or other high frequency information in a vibration signal. Typically, these methods further involve generating a lower frequency signal that quantifies the high frequency energy in the original signal, so that the lower frequency signal may be digitized and analyzed. Several of these techniques will be reviewed below.

So-called "shock pulse" analysis, developed by SPM Instrument AB of Sweden in the 1970's, uses a special transducer having a tuned resonant frequency at 32 kHz. Thus, this transducer is most sensitive to "shock pulse" signals in this frequency band, which are often indicative of bearing defects and poor lubrication. The output of the resonant transducer is reflective of energy in the frequency band of the transducer, and is used to develop a measure on a scale of 1 to 100 of the high frequency energy in the signal, with a value near 100 indicating a failure mode.

The Kurtosis method, developed by British Steel and the University of Southampton in the 1970's, applies a statistical method to isolated frequency bands, to develop a statistical parameter indicating the distribution of energy of the vibration signal in these various frequency bands. This analysis is typically performed on bands from 2.5–5.0 kHz, 5–10 kHz, 10–20 kHz, 20–40 kHz, 40–80 kHz, and a sum is generated of the Kurtosis parameters for each of the five bands to produce an overall measure of the high frequency content in the signal.

An enveloping process has been used by various predictive maintenance companies including Computational Systems Incorporated, SKF, and Diagnostics Instruments. In this process, the vibration signal is rectified and low-pass filtered, which has the effect of demodulating high frequency energy in the signal to base band; the amplitude of the resulting signal is reflective of high frequency energy in the signal prior to demodulation.

A final method, known as "spike energy detection" or alternatively "Peak Vue", has been used by the assignee of the present application as well as others to generate a measure of the high frequency energy in a vibration signal. FIG. 1 illustrates the typical analog circuit components that would be used for performing spike energy detection. In FIG. 1, the data collector has been configured for spike energy detection; thus, the electrical signal received from the vibration sensor is routed through analog switch 12 to high pass filter 14. As can be seen in FIG. 1, in a typical situation where the spike energy method would be useful, the transducer signal would include a low frequency vibration signal (seen in FIG. 1 as a sinusoidal waveform 16), superimposed with brief spikes of high frequency vibration 18. High pass filter 14 removes the low frequency sinusoidal waveform from the incoming vibration signal, and passes the higher frequency spikes 18, resulting in a signal as seen in FIG. 1 where the spikes 18 are superimposed upon a flat low frequency baseline signal 20.

The output of high pass filter 14, after passing through a second analog switch 22, is delivered through analog switch 24 to a decayed peak-to-peak detector 30. Detector 30 outputs a signal reflecting the peak-to-peak amplitude of the signal received at its input. This function is achieved by a combination of resistors and capacitors with op-amp circuits forming near-ideal diodes.

Specifically, a first portion of the detector 30 comprises capacitor C1, resistor R1 and an op-amp circuit that behaves as a near-ideal diode and is therefore illustrated as a diode D1. Through the action of diode D1, upon each negative voltage swing of the signal delivered to detector 30, capacitor C1 will accumulate a sufficient charge to have a peak voltage equal to the negative peak amplitude of the input signal. This charge will discharge from capacitor C1 through resistor R1 whenever the input signal is above its peak negative amplitude. The rate of discharge is determined by the time constant formed by multiplying R1 times C1. Typically, this time constant is chosen to approximate the reciprocal of the cutoff frequency of the high pass filter 14. As a consequence, only those frequencies of interest above the cutoff frequency will pass through capacitor C1 and be delivered to the second portion of detector 30.

The second portion of detector 30 comprises a second op-amp circuit that behaves as a buffer and near-ideal diode, and accordingly is illustrated as a buffer B1 and diode D2. The output of this op-amp circuit is delivered to a parallel connection of a capacitor C2 and resistor R2. Due to the presence of diode D2, capacitor C2 will he charged to the voltage across resistor R1 and diode D1 whenever that voltage is greater than the voltage currently across capacitor C2. Thus, capacitor C2 charges to a value representative of the peak-to-peak value of the input signal, comprised of the sum of the capacitor C1 voltage produced by the first portion of detector 30 and the positive peak amplitude of the input signal. Capacitor C2 discharges charge accumulated in this manner through resistor R2, at a rate determined by the time constant formed by multiplying R2 times C2. This time constant is normally chosen to be proportional to the period of repetition of the spikes in the input signal.

As a consequence of the long time constant R2C2, the waveform output from detector 30 has a sawtooth-like waveform 32 with a substantial low frequency component. This waveform call be readily digitized, and compared with previously recorded vibration signals and/or frequency transformed for analysis, as described above.

A difficulty inherent in the various high frequency energy detection methods described above is their lack of flexibility. In each of the above-described methods, specified frequency bands of the incoming vibration signal are isolated using special purpose analog circuitry. It different applications or different machines require the use of different frequency bands, redundant analog circuitry would need to be included in the data collector; i.e., the data collector would need to have multiple high pass filters and multiple peak-to-peak detectors, one for each frequency band of interest. Alternatively, the filters and detectors in the data collector may be made adjustable, but this would also require complexity, namely, in the filters and detectors, analog switches would need to be included to select between circuit components of different values, in order to change the frequency bands and time constants of the circuit. This approach may also encounter problems with noise due to the number of switches that are included in the analog signal path.

Accordingly, there is a need for a data collector and data collection method that is suitable for detection of high frequency energy in a signal, facilitating use in a wide range of applications.

SUMMARY OF THE INVENTION

In accordance with principles of the present invention, this need is met by a data collector having a digital signal processing circuit that receives a digitized vibration signal after the signal has been converted by an analog to digital converter to a digital form, and performs processing steps to isolate high frequency pulses in the digitized vibration signal and quantify energy content of those pulses. In accordance with principles of the present invention, the vibration signal is digitized by an analog to digital converter at a sampling rate that is sufficient to reproduce highest frequency of interest in the input signal. Then, the digital signal processing circuit performs high frequency pulse isolation and energy quantification upon tile resulting digital signal.

In the described embodiment, the digital signal processing circuit performs amplitude detection by detecting a peak-to-peak amplitude of the received vibration signal. Specifically, the digital signal processing circuit compares the digital signal to a peak negative value and when the signal exceeds the peak negative value the peak negative value is updated to be equal to the digital signal. Then, the digital signal processing circuit compares a maximum peak-to-peak value to the difference between the digital signal and the peak negative value, and if the difference is larger, the maximum peak-to-peak value is updated. Periodically, the maximum peak-to-peak value and peak negative value are reduced in magnitude by a decay factor, such that the peak negative value and maximum peak-to-peak value decay over time.

In this described embodiment, the maximum peak-to-peak value comprises a peak-detected digital output signal that may be stored and/or displayed to a user as a reflection of the high frequency content of the vibration signal. Furthermore, the digital signal processing circuit also performs a frequency transformation (e.g., a Fast Fourier Transform) upon the maximum peak to-peak-value to derive a spectrum for the maximum peak-to-peak value for storage and/or display to a user.

This digital methodology for high frequency analysis produces a resulting peak-detected output signal that is easily analogized to those produced using analog circuitry in known data collectors. Accordingly, users that are knowledgeable in the analysis of peak-detected waveforms produced by prior data collectors, may readily reapply this knowledge to the peak-detected digital output signal produced in accordance with principles of the present invention.

It is a significant aspect of the present invention that the decay factors used in computing the maximum peak-to-peak value and peak negative value are determined by the digital signal processing circuit and may be readily changed. As a consequence, high frequency processing performed by the digital signal processing circuit may be readily adapted to the particular frequency characteristics of the machine being analyzed for predictive maintenance. Importantly, this adaptation may be made without any modification to the analog circuitry of the data collector.

In the described embodiment, the digital signal processing circuit is in the form of a software programmable processor performing a software-defined signal processing procedure to implement the methods described above. In this embodiment, adjustment of parameters is further simplified by adapting the software-defined procedure to obtain these parameters from a storage location, and to permit a user to define these parameters as desired.

The above and other objects and advantages of the present invention shall be made apparent from the accompanying drawings and the description thereof.

BRIEF DESCRIPTION OF THE DRAWING

The accompanying drawings, which are incorporated in and constitute a part of this specification, illustrate embodiments of the invention and, together with a general description of the invention given above, and the detailed description of the embodiments given below, serve to explain the principles of the invention.

FIG. 1 is a block diagram of a conventional data collector including spike energy analog signal processing circuitry;

FIG. 2 is a block diagram of a data collector in accordance with principles of the present invention for performing digital signal processing of high frequency energy in a vibration signal;

FIG. 4 is a flow chart of operations performed by the digital signal processor of claim 2 in processing high frequency energy in a vibration signal in accordance with principles of the present invention.

DETAILED DESCRIPTION OF SPECIFIC EMBODIMENTS

Figure 3:
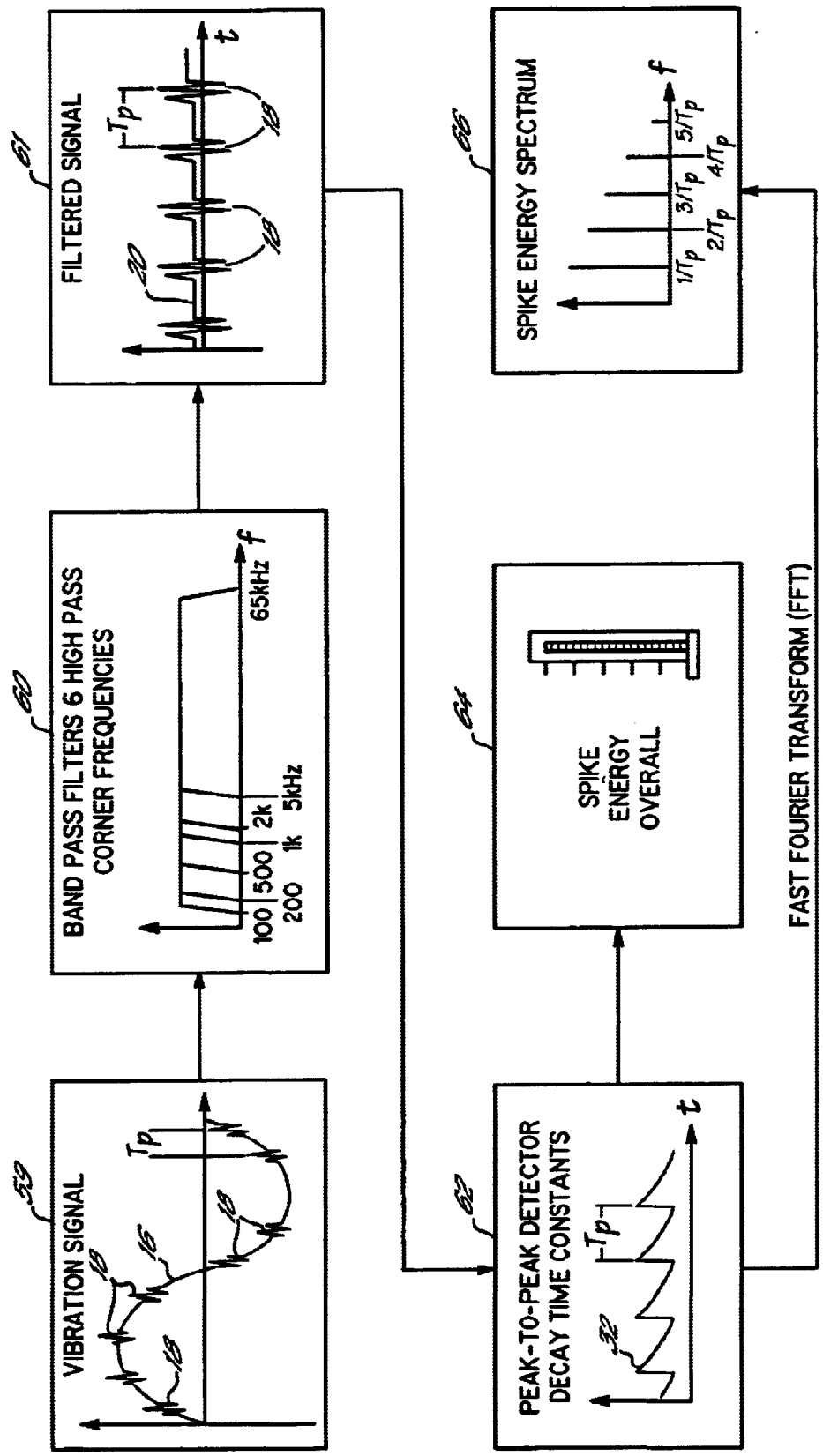
FIG. 3 is a process diagram illustrating the processing steps carried forward by the digital signal processor illustrated in FIG. 2.

Referring now to FIG. 2, a data collector 40 in accordance with principles of the present invention can be described. Functional blocks of the data collector are illustrated in FIG. 2 to facilitate the description of the operations contemplated by the present invention. It will be appreciated, however, that a data collector suitable for carrying out the principles of the present invention may take many forms. In one embodiment, a suitable data collector comprises a data collector available from the assignee of the present invention under the model name dataPAC 1500. Another suitable data collector is disclosed in U.S. Pat. No. 5,633,811 issued to Canada et al., and assigned to Computational Systems Incorporated, which describes a data collector sold by Computational Systems Incorporated, the disclosure of which is incorporated herein by reference. Alternatively, another suitable data collector is a palmtop computer having a sound interface card therein for receiving digital vibration data such as is disclosed in U.S. Pat. No. 5,808,903 issued to Schiltz et al. and assigned to the assignee of the present application, the disclosure of which is also incorporated herein by reference.

Regardless of the embodiment of data collector that is utilized, the data collector will comprise analog signal processing circuits 42 for receiving a signal from a vibration sensor such as a piezoelectric accelerometer and conditioning this signal for sampling and conversion to a digital format. The operations performed by circuits 42 may include gain and offset collection and various filtering operations, as well as low pass filtering for anti-aliasing.

An analog to digital (A/D) converter 44 receives the output of signal processing circuits 42 and converts this analog signal to a digitized form A/D converter 44 is a high sampling rate high resolution data converter programmed to sample its analog input signal at a sampling rate at least twice the maximum frequency of interest in the vibration signal. A suitable A/D converter for this purpose is sold by Burr-Brown as part no. DSP 101 or DSP 102.

The digitized vibration signal generated by A/D converter 44 is delivered to a digital signal processor 46. Digital signal processor 46 may comprise a special purpose digital signal processor operating under the control of suitable software, a general purpose microprocessor operating under the control of suitable software, or a discrete logic circuit for processing digital signals in the manner described below. Each of these embodiments is within the scope of the present invention, however, the following description will focus upon embodiments of tile invention in which digital signal processor 46 is a programmable circuit operating under the control of software.

Processor 46 is coupled to a keypad and display 48 for interacting with a user of the data collector 40. Keypad and display may comprise the keypad and display incorporated into a laptop computer or the touch screen incorporated into a palmtop computer, or a custom display and surrounding function keys on a special purpose data collector.

Processor 46 is further coupled to a storage device 50 for storing digital data, including (where processor 46 is a programmable circuit) software for operating the processor to carry out the methods of the present invention, as well as stored digitized vibration signals and/or processed versions thereof.

Storage device 50 and processor 46, or either of them, may optionally interface through a host interface circuit 52 to deliver stored data from storage device 50 to a host computer 54. Host computer 54 may include software for evaluating or archiving digital signals stored by the data collector 40. In such an embodiment, some or all of the analysis steps described in connection with FIG. 3 may be performed in a host computer upon digital data stored by data collector 40. Alternatively, data collector 40 may include sufficient processing power and digital storage to fully process and archive digital signals collected by the data collector, in which case host interface 52 and host computer 54 may not be needed. While both embodiments are within the scope of the present invention, the following discussion will focus upon embodiments of the invention in which digital signal processor 46 is a programmable circuit operating under the control of software.

Host interface 52 may take any of a variety of forms, including a serial interface such as RS-232 or USB coupled to a PC, an Ethernet or other network connection connected through network cabling, a parallel port connection, or other suitable forms. Furthermore, host computer 54 may comprise a palmtop, laptop, or desktop PC, or a mono- or multi-processor server.

Referring now to FIG. 3 an explanation can be given of steps performed by the data collector and/or host computer of FIG. 2, in accordance with principles of the present invention. A digitized vibration signal 59 delivered by A/D converter 44 to digital signal processor 46 that is a good candidate for high frequency processing is illustrated in FIG. 3. This signal 59 comprises a low frequency vibration signal (seen in FIG. 3 as a sinusoidal waveform 16), superimposed with brief spikes of high frequency vibration 18.

Digital signal processor 46 performs an initial routine for filtering and optionally decimating the digitized signal. Specifically, processor 46 performs a digital signal processing routine upon the received digital signal that implements a low-pass or band-pass filter. As illustrated at 60 in FIG. 3 this filtering routine may be responsive to stored parameters available to software in processor 46 to select a desired frequency band of interest, e.g., the filter may be a band-pass filter having a lower cutoff frequency selectable between 100 Hz, 200 Hz, 500 Hz, 1 kHz, 2 kHz and 5 kHz, and an upper cutoff frequency of 65 kHz. Other frequency bands may also be utilized for different applications. Essentially, the lower cutoff frequency must be above the fundamental machine vibration frequency that is reflected by the sinusoidal low frequency signal 16 received by digital signal processor 46. The upper cutoff frequency must be at a sufficiently high frequency to allow the brief spikes 18 of high frequency signal to be passed with minimal attenuation or distortion. The upper cutoff frequency is also limited by the analog anti-alias filtering that is performed on the signal prior to A/D conversion. In the illustrated embodiment, the upper cutoff frequency is 65 kHz.

Band pass filtering performed by processor 46 removes the low frequency sinusoidal waveform 16 from the incoming vibration signal, and passes the higher frequency spikes 18, resulting in a signal 61 as seen in FIG. 3 where the spikes 18 are superimposed upon a flat low frequency baseline signal 20.

Having thus isolated the high frequency spikes through band pass filtering, in a second processing step, digital signal processor 46 performs a digital signal processing routine, described in greater detail below with reference to FIG. 4, to generate a peak-to-peak detected signal. The peak-to-peak detection signal processing routine includes decay time constants causing the resulting waveform to have a sawtooth-like waveform 32 with a substantial low frequency component. This sawtooth-like digital signal waveform is analogous to the analog signal produced using analog circuitry in known data collectors. Accordingly, it can be processed in an analogous manner by displaying its average amplitude or time waveform as depicted at 62 or 64 in FIG. 3, or by performing a Fast Fourier Transform other frequency transform and displaying the energy spectrum for the signal as depicted at 66 in FIG. 3. Users that are knowledgeable in the analysis of peak-detected waveforms produced by prior data collectors, and in their amplitude, time and frequency domain appearance, may readily reapply this knowledge to the peak-detected digital output signal produced in accordance with principles of the present invention to perform predictive maintenance analysis.

Referring now to FIG. 4, the process performed by the digital signal processor 46 in processing a vibration signal in response to user input can be explained in greater detail. In a first step 70, a user of the system identifies band pass frequencies for the digital band pass filtering illustrated at 60 in FIG. 3. Specifically, the user specifies a lower cutoff frequency, e.g., by selecting one of 100 Hz, 200 Hz, 500 Hz, 1 kHz, 2 kHz or 5 kHz, and optionally selects an upper cutoff frequency. In step 70, the user also identifies the expected frequency fD at which a defect signal is likely to be seen, and the number of harmonics, n, of this expected frequency that are of interest for display and analysis. The upper cutoff frequency, if it is specified by the use, must be large enough to pass all of the brief spikes 18, and a confirmation of this may be included in step 70.

In a subsequent step 72, this user-provided information is used to compute parameters for the digital processing that is performed in the subsequent processes. Specifically, these parameters include a time constant $\tau 1$ and a second time constant $\tau 2$. The time constant $\tau 1$ is computed as 0.000324 seconds when the user specifies in step 70 a lower bandpass cutoff frequency of 2 kHz or 5 kHz, and $\tau 1$ is computed as 0.0069 seconds when the user specifies in step 70 a lower bandpass cutoff frequency of less than or equal to 1 kHz. The time constant $\tau 2$ is computed as $2.07/(2*\pi*fD)$ or $2.07*n/(2*\pi*fmax)$.

As will be appreciated, the first formula $\tau 2$ time constant establishes an appropriate decay rate to display the desired defect frequency fD at near maximum amplitude, whereas the second formula for the $\tau 2$ time constant ensures that n harmonics of the defect frequency fD will be displayed, where fmax is the maximum frequency that will be captured by the A/D converter.

After computing these parameters in step 72, digital processing commences. First, in step 74, values for the peak negative sample and the maximum peak to peak value are initialized at zero. Then, in step 76, the digitized vibration signal is received from the A/D converter 44. The signal is then band-passed filtered in step 78 by applying the band-pass filtering algorithm with the frequencies specified in step 70. The resulting filtered stream of samples are received by a peak detection algorithm. In step 80, a sample is received, and in a loop comprising steps 82, 84, 86, 88, 90 and 92, this sample is processed. Thereafter, in step 96 a subsequent sample is received, and processing returns to step 82 to process the new sample.

In the first step 82 of the loop identified above, the current sample is evaluated to determine whether it is mole negative than the stored peak negative sample. If so, then in step 84 the peak negative sample is replaced with the current sample value. As a consequence the peak negative sample will always have the most negative sample that has been previously encountered, or a decayed version thereof.

If in step 82 tile current sample is not more negative than the peak negative sample, processing continues to step 86 in which the difference between the current sample and the peak negative sample is computed, and compared to the stored decayed maximum peak to peak value. If the current difference is larger than the stored decayed maximum peak to peak value, then in step 88 the stored decayed maximum peak to peak value is replaced with the current difference. As a consequence, the stored decayed maximum peak to peak value will always reflect the largest decayed peak-to-peak value of the incoming samples that has been previously encountered.

After step 84 or 88, or immediately after step 86 if the current difference is less than the stored maximum peak to peak value, processing continues to steps 90 and 92, in which steps are taken to apply the decay time constants $\tau 1$ and $\tau 2$ to the stored peak negative value and maximum peak to peak value. Specifically, in step 90, the peak negative sample is multiplied by a factor $\exp(-T/\tau 1)$, where exp( ) represents the natural exponential operation, aid T is the time period between digital samples. Similarly, in step 92, the maximum peak to peak value is multiplied by a factor $\exp(-T/\tau 2)$.

It will be appreciated that these operations cause the peak negative value and maximum peak to peak value to decay over time with an exponential decay characteristic having the time constants $\tau 1$ and $\tau 2$, respectively.

After step 92, in addition to receiving a new sample value in step 96, other operations are performed upon the computed value for the maximum peak to peak value. Specifically, in step 94, the decayed maximum peak to peak value computed in the preceding steps is delivered to subsequent processes that display a spike energy time waveform, or compute a Fast Fourier Transform of the decayed maximum peak to peak value to generate a spectral display. The resulting time and spectral displays are analogous to those produced by prior instrumentation utilizing solely analog spike energy detection circuitry, and thus can be utilized readily by those persons experienced in using prior analog spike energy detection circuitry.

The decayed maximum peak to peak value is also used in step 98 to compute an "overall" spike energy value, analogous to that created by some prior data collectors. In prior data collectors sold by the assignee of the present application, the "overall" spike energy value is created by an analog spike energy circuit. In this circuit, the time constant of the RC filter formed by capacitor C2 and resistor R2 of FIG. 1, is 0.03 seconds. The output of the spike detection circuit is then fed through a low pass filter having a cutoff at 0.1 Hz. The resulting essentially DC value indicates the "overall" energy of spikes in the input signal. To produce an analogous signal using the present invention, a compensation is performed to correct the time constant $\tau2$; specifically, $\tau2$ is corrected such that it is no less than 0.03 seconds. To do this, if $\tau2$ is less than 0.03 seconds, in step 98 the maximum peak to peak value is multiplied by a compensatory factor equal to $$\exp(-T/(0.03-\tau2))$$

The combined effect of this compensatory factor and the factor used in step 92 is equal to multiplying the maximum peak to peak value by a factor of $\exp(-T/0.03)$. Thus, if the value of $\tau2$ is less than 0.03 seconds, the compensatory step 98 adjusts the maximum peak to peak value to simulate a $\tau2$ of 0.03 seconds.

After the compensation of step 98 is performed, as needed, in step 100 the resulting maximum peak-to-peak value samples are fed to a digital low pass filtering process, having a cutoff frequency at 0.1 Hz. This is analogous to the low pass filtering used to compute "overall" spike energy values in prior data collectors. Then, the resulting low pass filtered samples are displayed, as a DC value, to indicate the "overall" spike energy in the received vibration signal. This "overall" value is readily analogous to those generated by prior data collectors and can therefore be readily used by those persons experienced with the analogous values generated by data collectors having analog peak detection functions.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concepts.

What is claimed is:

1. A data collector for detecting and quantifying high frequency energy in a received signal, comprising
   an analog to digital converter converting said received signal to a digitized signal at a sampling rate that is sufficient to reproduce a highest frequency of interest in said received signal, and
   a digital signal processing circuit that receives said digitized signal and performs processing steps to isolate high frequency pulses in the digitized signal from lower frequency components of the digitized signal, and process said high frequency pulses by forming a time-varying peak-detected signal from said high frequency pulses, the time variation of the peak-detected signal corresponding to time variation of peak amplitudes of the high frequency pulses, to quantify energy content of the isolated pulses.

2. A data collector for detecting and quantifying high frequency energy in a received vibration signal from a rotating machine, comprising
   an analog to digital converter converting said received vibration signal to a digitized vibration signal at a sampling rate that is sufficient to reproduce a highest frequency of interest in said received vibration signal, and
   a digital signal processing circuit that receives said digitized vibration signal and performs processing steps to isolate high frequency pulses in the digitized vibration signal from lower frequency components of the digitized signal, and process said high frequency pulses to quantify energy content of the isolated pulses and evaluate the potential for mechanical faults in the rotating machine.

3. The data collector of claim 1 said digital signal processing circuit detects a peak-to-peak amplitude of said digitized signal by comparing a current sample of said digitized signal to a peak value and when the excursion of said current sample from zero exceeds said peak value then said digital signal processing circuit updates said peak value to be equal to said current sample.

4. The data collector of claim 3 wherein said peak value is a peak negative value and said digital signal processing circuit detects a peak-to-peak amplitude of said digitized signal by comparing a maximum peak-to-peak value to a difference between said current sample and said peak negative value, and if the difference is larger, updating said maximum peak-to-peak value.

5. The data collector of claim 3 wherein said digital signal processing circuit periodically reduces said peak value of said digitized signal by a factor such that said peak value decays over time.

6. The data collector of claim 5 wherein said digital signal processing circuit is responsive to user input to alter said factor, whereby quantification of high frequency energy content by said digital signal processing circuit can be adapted to frequency characteristics of said signal.

7. The data collector of claim 6 wherein said digital signal processing circuit comprises a software programmable processor performing a software-defined signal processing procedure, said software-defined procedure adapted to obtain said factor from a storage location, and to permit a user to define said factor and store said factor in said storage location.

8. The data collector of claim 1 wherein said digital signal processing circuit detects a peak-to-peak amplitude of said digitized signal and periodically reduces said peak-to-peak amplitude of said digitized signal by a factor such that said maximum peak-to-peak amplitude decays over time.

9. The data collector of claim 8 wherein said digital signal processing circuit is responsive to user input to alter said factor, whereby quantification of high frequency energy content by said digital signal processor can be adapted to frequency characteristics of said signal.

10. The data collector of claim 9 wherein said digital signal processing circuit comprises a software programmable processor performing a software-defined signal processing procedure, said software-defined procedure adapted to obtain said factor from a storage location, and to permit a user to define said factor and store said factor in said storage location.

11. The data collector of claim 3 further comprising a storage device, said digital signal processing circuit storing said maximum peak-to-peak value in said storage device.

12. The data collector of claim 3 further comprising a display, said digital signal processing circuit displaying said maximum peak-to-peak value on said display.

13. The data collector of claim 3 wherein said digital signal processing circuit further performs a frequency transformation upon the maximum peak-to-peak value to derive a spectrum for the maximum peak-to-peak value.

14. The data collector of claim 13 wherein said frequency transformation is a Fast Fourier Transform.

15. The data collector of claim 1 wherein said digital signal processing circuit comprises a software programmable processor performing a software-defined signal processing procedure.

16. A method of detecting and quantifying high frequency energy in a received signal, comprising converting said received signal to a digitized signal at a sampling rate that is sufficient to reproduce a highest frequency of interest in said received signal, and receiving said digitized signal, isolating high frequency pulses in the digitized signal from lower frequency components of the digitized signal, and processing said high frequency pulses by forming a time-varying peak-detected signal from said high frequency pulses, the time variation of the peak-detected signal corresponding to time variation of peak amplitudes of the high frequency pulses, to quantify energy content of the isolated pulses.

17. A method for detecting and quantifying high frequency energy in a received vibration signal from a rotating machine, comprising converting said received vibration signal to a digitized vibration signal at a sampling rate that is sufficient to reproduce a highest frequency of interest in said received vibration signal, and receiving said digitized vibration signal, isolating high frequency pulses in the digitized vibration signal from lower frequency components of the digitized signal, and processing said high frequency pulses to quantify energy content of the isolated pulses and evaluate the potential for mechanical faults in the rotating machine.

18. The method of claim 16 further comprising detecting a peak-to-peak amplitude of said digitized signal by comparing a current sample of said digitized signal to a peak value, and when the excursion of said current sample from zero exceeds said peak value, updating said peak value to be equal to said current sample.

19. The method of claim 18 wherein said peak value is a peak negative value and a peak-to-peak amplitude of said digitized signal is detected by comparing a maximum peak-to-peak value to a difference between said current sample and said peak negative value, and if the difference is larger, updating said maximum peak-to-peak value.

20. The method of claim 18 further comprising periodically reducing said peak value of said digitized signal by a factor such that said peak value decays over time.

21. The method of claim 20 further comprising responding to user input to alter said factor, whereby quantification of high frequency energy content can be adapted to frequency characteristics of said received signal.

22. The method of claim 21 further comprising
obtaining said factor from a storage location, and
permitting a user to define said factor and store said factor in said storage location.

23. The method of claim 16 further comprising detecting a maximum peak-to-peak amplitude of said digitized signal, and periodically reducing said maximum peak-to-peak amplitude of said digitized signal by a factor such that said maximum peak-to-peak amplitude decays over time.

24. The method of claim 23 further comprising responding to user input to alter said factor, whereby quantification of high frequency energy content can be adapted to frequency characteristics of said digitized signal.

25. The method of claim 24 further comprising
obtaining said factor from a storage location, and
permitting a user to define said factor and store said factor in said storage location.

26. The method of claim 16 further comprising storing said a maximum peak-to-peak value in a storage device.

27. The method of claim 16 further comprising displaying a maximum peak-to-peak value on a display.

28. The method of claim 16 further comprising performing a frequency transformation upon the peak-detected signal to derive a spectrum for the peak-detected signal.

29. The method of claim 28 wherein said frequency transformation is a Fast Fourier Transform.

30. The data collector of claim 5 wherein said digital signal processing circuit automatically computes said factor so that quantification of high frequency energy content by said digital signal processing circuit is adapted to frequency characteristics of said digitized signal.

31. The method of claim 20 further comprising automatically computing said factor so that quantification of high frequency energy content is adapted to frequency characteristics of said digitized signal.

* * * * *

UNITED STATES PATENT AND TRADEMARK OFFICE
CERTIFICATE OF CORRECTION

| | | |
|---|---|---|
| PATENT NO. | : 6,868,348 B1 | Page 1 of 1 |
| APPLICATION NO. | : 09/430077 | |
| DATED | : March 15, 2005 | |
| INVENTOR(S) | : Donn V. Stoutenberg and Ming Xu | |

It is certified that error appears in the above-identified patent and that said Letters Patent is hereby corrected as shown below:

Column 1, line 22, delete "identify an variations", insert --identify variations--.

Column 2, line 32, after "bands", the sentence beginning with "This analysis" should immediately follow, no paragraph indentation is required.

Column 3, line 48, delete "circuitry. It different", insert --circuitry. If different--.

Column 4, line 14, delete "upon tile resulting", insert --upon the resulting--.

Column 5, line 67, delete "form A/D", insert --form. A/D--.

Column 6, line 5, delete "of tile invention", insert --of the invention--.

Column 7
Line 28, delete "Transform other", insert --Transform or other--.
Line 49, delete "the use, must", insert --the user, must--.

Column 8
Line 19, delete "is mole negative", insert --is more negative--.
Line 25, delete "82 tile current", insert --82 the current--.
Line 47, delete "aid T", insert --and T--.

Column 10, Claim 3, line 1, delete "claim 1 said", insert --claim 1 wherein said--.

Column 12, Claim 26, lines 1-2, delete "storing said a maximum", insert --storing a maximum--.

Signed and Sealed this

Fifteenth Day of August, 2006

JON W. DUDAS
*Director of the United States Patent and Trademark Office*